United States Patent [19]

Parviainen et al.

[11] Patent Number: 5,331,851
[45] Date of Patent: Jul. 26, 1994

[54] METHOD FOR MEASURING THE WORKING CONDITION OF MUSCLES AND MEASURING AND TRAINING SYSTEM FOR MEASUREMENTS OF THE WORKING CONDITION OF MUSCLES AND FOR MUSCLE TRAINING

[75] Inventors: Arno Parviainen, Vantaa; Jukka Lyömiö, Espoo, both of Finland

[73] Assignee: David Fitness & Medical Ltd. Oy, Vantaa, Finland

[21] Appl. No.: 761,986

[22] PCT Filed: Mar. 23, 1990

[86] PCT No.: PCT/FI90/00077

§ 371 Date: Sep. 23, 1991

§ 102(e) Date: Sep. 23, 1991

[87] PCT Pub. No.: WO90/11049

PCT Pub. Date: Oct. 4, 1990

[30] Foreign Application Priority Data

Mar. 23, 1989 [FI] Finland .................................. 891420

[51] Int. Cl.$^5$ ................................................ A61B 5/00
[52] U.S. Cl. ................................. 73/379.010; 601/23
[58] Field of Search .......................... 73/379, 380, 381;
364/413.02, 413.04; 482/900, 901, 902, 903, 6;
128/25 R

[56] References Cited

U.S. PATENT DOCUMENTS

| | | | |
|---|---|---|---|
| 4,571,682 | 2/1986 | Silverman et al. | 482/902 |
| 4,702,108 | 10/1987 | Amundsen et al. | 73/379 |
| 4,779,865 | 10/1988 | Lieberman et al. | 482/8 |
| 4,805,455 | 2/1989 | Delgiorno et al. | 73/379 |
| 4,817,940 | 4/1989 | Shaw et al. | 482/902 |
| 4,869,497 | 9/1989 | Stewart et al. | 482/902 |
| 4,905,676 | 3/1990 | Bond et al. | 482/902 |
| 4,912,638 | 3/1990 | Pratt, Jr. | 482/902 |
| 4,921,244 | 5/1990 | Berroth | 73/379 |

FOREIGN PATENT DOCUMENTS 3509693 9/1987 Fed. Rep. of Germany .

*Primary Examiner*—Richard E. Chilcot, Jr.
*Assistant Examiner*—R. Biegel
*Attorney, Agent, or Firm*—Kane, Dalsimer, Sullivan, Kurucz, Levy, Eisele and Richard

[57] ABSTRACT

The invention relates to a method for measuring the working condition of muscles, and to a measuring and training system for measuring the working condition of muscles and muscle training. Muscles are loaded with mechanical devices, the working condition of muscles is measured with measuring equipment, and the obtained results are registered. According to the invention, from among a number of separate, independent muscle training devices, there is chosen one, whereby the muscles are loaded, and the working condition of muscles is measured by means of the sensors provided therein. The sensors of the training device are connected, by means of a connector element, to a data processing unit, and the chosen type of training device is identified to the data processing unit, whereafter the measuring program, corresponding to the training device in question, is activated. From the measuring program, including a number of measuring steps, there is chosen the desired step, the initial settings whereof are determined for each person individually.

18 Claims, 9 Drawing Sheets

METHOD FOR MEASURING THE WORKING CONDITION OF MUSCLES AND MEASURING AND TRAINING SYSTEM FOR MEASUREMENTS OF THE WORKING CONDITION OF MUSCLES AND FOR MUSCLE TRAINING

The present invention relates to a method for measuring muscular functionality. By muscular functionality is meant the working condition of muscles.

The present invention also relates to a measuring and training system for measuring muscular functionality and for muscle training.

In the prior art there are known methods for measuring muscular functionality, utilizing integrated systems which include mechanical devices for straining muscles, connected measuring equipment and a data processing unit, whereto the measuring results are transferred and processed therein, and output equipment.

Muscular functionality is measured with mechanical devices, which are essential and inseparable elements in the measuring system. The said mechanical devices comprise a lever arm connected to a dynamometer, such as a mechanical gyroscope arrangement, the velocity of which lever arm can be limited in a desired fashion. In addition to this, the mechanical equipment includes an adjustable seat or chair, to the frame whereof the dynamometer can be attached. By means of different auxiliary elements, the lever arm can be connected to the extremities, trunk or part of the trunk of the person in question, in order to measure and train the various muscles in these parts of the body.

Muscular functionality is measured so that the angular velocity of the path of motion is, prior to the measurement, adjusted to a standard value, whereafter the person in question pushes the lever arm with the muscles under examination. When the pushing is stopped, the lever arm stops, adjusted by the dynamometer, without straining the muscles to be used. Thus the lever arm does not strain the muscles, but the muscles themselves create the load. This principle of measurement is called the isokinetic principle.

The obtained results are fed into a data processing unit, whereby for instance the torques of the muscles under examination are calculated at a chosen angular velocity. The results are furnished through an output device, such as a printer or a monitor, either as digital data or as graphic curves.

A problem with the prior art methods and arrangements is that by means of mainly one mechanical device, comprising one lever arm, there is performed the measuring and training of practically all possible muscle groups. The adjusting and focusing of the position of the lever is cumbersome and complicated, and often the connecting of the muscle group under examination to the lever arm does not succeed in a similar fashion as for instance in the previous measurement of the same person. As a result, the measurements are not fully comparable with each other. Moreover, the motions performed by the muscles are not ergonomically or biomechanically correct, because the connecting of the lever arms and the muscle groups under examination is difficult owing to the reasons stated above.

Another problem with the known systems is that the system as a whole is reserved for one single person only, both during the measurement and during the training. When the fact that the systems are expensive is taken into account, the efficiency and the degree of utilization can be considered poor.

Yet another problem with the current measuring methods is that the readings obtained in the measurements are not compatible with any existing method of training.

The current measuring methods also have the drawback that on the basis of the measurements it is only possible to find out whether the strength level of the person has gone up, but on the basis of the results it is not possible to define for instance training loads for training.

Yet another problem is that the measurements with the mechanical devices of the measuring system are generally carried out in different positions than in the training exercise proper, which is normally performed with a separate exercise device. When the measurement is carried out in a different environment and conditions than the training exercise, both the measurement and the exercise are performed inadequately.

A further problem with the prior art measuring methods and systems is the difficulty to use them. The measuring programmes stored in the computer units are complex multilayer programmes, and the number of alternatives to be chosen is so large, that the learning of the measuring methods and systems is toilsome and their use inconvenient. Normally a highly educated personnel is required in order to carry out the measurements.

Yet another problem with the current methods and systems for measuring muscular functionality is the isokinetic principle. Results obtained from measurements performed on the basis of this principle include many uncontrollable variables, wherefore the results are not considered reliable. Moreover, an exercise device realized according to the isokinetic principle can be regarded unphysiological; only about 20% of the muscular motion in a normal situation takes place at a standard velocity, whereas the first part of the motion is accelerating and the final part slowing motion. Also the fact that the method only works during a so-called positive motion, i.e that it provides resistance only during a concentric contraction but not during an eccentric contraction, when for example a load is normally lowered down, can be considered as a drawback in the methods and systems applying the isokinetic principle.

Furthermore, a problem with the known methods and systems applying the isokinetic principle is that the performed measurements are one-sided. Generally the systems measure muscular strength as a function of the angle of motion. Measuring systems perform measurements of muscular strength, and data processing units are used for defining the level of strength of the person. Generally speaking, the obtained information is limited. Neither do the systems allow for any proper analysis of the results.

Yet another problem with the current systems is that the measuring results are obtained in a form difficult to read. Often the print resembles a journal tape and is very hard to understand. If a display unit is used, the results are given for instance as successive or consecutive graphic curves which are difficult to compare with each other.

The object of the present invention is to eliminate the above mentioned drawbacks.

In the method of the present invention for measuring muscular functionality, muscles are loaded by means of mechanical devices, the muscular functionality is measured and the obtained results are registered. The invention is characterized in that from among a number of different and independent muscle training devices there is chosen a specific device, whereby the muscles under measurement are loaded and their functionality measured; the said training device is connected to a data processing unit; the training device is identified; the measuring programme, corresponding to the training device in use, is activated; from the measuring programme including a number of measuring steps there is chosen the desired step, the initial settings whereof are defined individually for each person.

In a preferred embodiment of the method, the load of the training device is formed of a counterbalance weight, and the muscles are loaded, by intermediation of a movable lever arm, with the counterbalance weight so that the transition velocity of the lever arm is free, i.e. it can be determined by means of the muscles. Thus the mechanical device is the training device which functions according to the dynamic principle.

In another preferred embodiment of the method, the measuring steps include a range of motion measurement, an isometric force measurement and a fatigue test, in which range of motion measurement the ranges of motion of the muscles are measured as rotation angles, in the isometric measurement the torque, and particularly the maximum torque is measured, and in the fatigue test the muscles are strained by a standard load.

In another preferred embodiment of the method, the isometric force measurement is carried out in a static fashion so that the lever arm is kept in a predetermined angular position, and while exerting the muscles, the torque directed to the lever arm is measured.

In another preferred embodiment of the method, the measuring of the torque is carried out for the duration of a given period after the torque directed to the lever arm has exceeded the preset limit value, and the peak average for the torque, i.e. the maximum torque, is then calculated.

In another preferred embodiment of the method, the fatigue test is carried out dynamically by a chosen standard load, so that for the test a reference velocity is chosen from among a number of predetermined angular velocities, whereafter the said reference velocity is illustrated visually, and the test is performed by straining the muscles according to this velocity.

In another preferred embodiment of the method, the fatigue test is carried out statically by means of a chosen standard load, so that this standard load is maintained, by means of the muscles, in a predetermined position, and the torque is measured.

In another preferred embodiment of the method, the load of the fatigue test is chosen on the basis of an isometric force measurement, so that it corresponds to a given portion of the maximum torque.

In another preferred embodiment of the method, the muscular EMG activity is measured simultaneously with the performed measuring step.

In another preferred embodiment of the method, the obtained results are displayed in real time on a monitor screen.

In another preferred embodiment of the method, the obtained results are viewed in a display unit by rescaling the measurement at the desired point.

In another preferred embodiment of the method, in addition to the measuring programme, there can be chosen, according to the special needs, optional special functions for carrying out: measurement series, where the measuring steps of the measuring programme are defined beforehand, and performed thereafter successively in series; entering new operational data; updating personal data; service tests for the measuring equipment; calibration of the sensors; listings of the measuring results; comparison of the results obtained in different measurements; re-examination and evaluation of the obtained results, as well as the selection of the language to be used.

The measuring and training system of the present invention for measuring muscular functionality and for muscle training comprises mechanical devices for loading the muscles, measuring devices for measuring the muscular functionality, a data processing unit whereto the obtained results are transferred and whereby they are analysed, and an output device, such as a display unit and a printer, for displaying the data connected to the measuring process. The mechanical devices of the invention are training devices, which are indpendent, separate units provided with sensors; and the system is provided with a connector element, which is connected to the data processing unit, and whereto the sensors of the training device in question are connectable; and with identification means, whereby the type of the training device is identified, and the measuring programme is chosen according to the said type.

In a preferred embodiment of the system, the training device includes a counterbalance weight, which serves as a load and has optional sizes, and at least one lever arm, which is moved with the muscles to be measured, and which lever arm is connected to the counterbalance weight by a transmission assembly.

In another preferred embodiment of the system, the connector element includes an analog to digital, or an A/D converter, and a processor, and through the said A/D converter the analogical sensors are connectable to the processor, which is connected, via isolators such as optoisolators, to the data processing unit. The digital sensors are most advantageously connected directly to the processor.

In another preferred embodiment of the system, the connector element is an independent device, which can be detachably fastened to the training device.

In another preferred embodiment of the system, the training device is provided with a nest wherein the connector element can be installed, and which nest and connector element include matching coupling members for connecting the sensors electrically to the connector element. Naturally the connector element can be installed in connection with the training device in some other detachable fashion, too.

In another preferred embodiment of the system, the indentification means are formed of a number of mechanically interconnectable parts, which are arranged in the connector element and the training device, and whereby the training device can be identified. The identification takes place by means of a special code, which can be mechanical and/or electric. The code is read, by the aid of the connector element, automatically when the connector element is connected to the training device, and consequently the training device is identified.

In another preferred embodiment of the system, the sensors of the training devices include load sensors, such as strain gauge sensors, and range of motion sensors, such as angle sensors. Generally the strain gauge sensors are analogical, whereas the angle sensors are advantageously digital.

In another preferred embodiment of the system, the connector element also is provided with a number of sensors measuring EMG, or electric activation of the muscles.

An advantage of the present invention is that the measurements are carried out with similar training equipment as the training proper. Among the various independent training devices, there is each time chosen the most suitable, whereby certain muscles can be both measured and trained.

Another advantage of the invention is that the chosen training device is automatically identified, and the corresponding measuring programme also is automatically started after identifying the training device. Proceeding to the selection and performing of the measuring process proper takes place rapidly and easily.

Another advantage of the invention is that the measuring method and system are straightforward and simple to use.

A further advantage of the invention is that the measuring steps are defined simply and clearly, so that they can be performed reliably and in a similar fashion each time. The measuring steps can be supervised more accurately than before.

Yet another advantage of the invention is its versatility. On the basis of the method and system, it is possible to create various applications from scientific study to day-to-day training.

Another advantage of the invention is that from the measuring results, the load and duration of the exercise required in the training of muscular fitness are obtained by immediate calculation. The exercise is defined accurately and smoothly, without uncertainty and guesswork. The exercises connected to the training can be determined correctly, based on the strength level, fitness and muscular type of the person in question, and individual development can be accurately followed with repeated measurements.

Another further advantage of the invention is that the measurements are based on the use of such exercise devices that follow the dynamic principle. This is of utmost importance, particularly as regards training, because thus the muscles undergo a remarkably more efficient and stimulating influence than with equipment based on the isokinetic principle. The muscles are strongly activated along the whole path of motion.

Another advantage of the invention is that the system is easily assembled. The system of the present invention is based on modularity and decentralization. The system comprises independent mechanical training devices and a data processing unit, which can be connected to any of the training devices. The training of muscular fitness can be carried out with any of the independent training devices without the data processing unit, but if the person is desired to be measured, the data processing unit is brought to beside the training device, and by means of the connector element, the training device and the data processing unit are interconnected. Only a swift operation is needed to connect the training device to become a part of a versatile measuring system.

Another advantage of the invention is that individuals can be examined and measured in a concentrated fashion for example in hospitals which are provided with the whole system. The training programme for an individual is planned on the basis of the results from the measurement, whereafter for example a person to be rehabilitated is sent near his home to a physical therapy station provided with training equipment fully compatible, i.e. similar, to the measuring system. Thus the training of muscular fitness is carried out locally, and from time to time the person is sent to the hospital for measurements. From the point of view of the individual, the measuring and training take place in similar fashion.

Another additional advantage of the invention is that the system can be expanded in an easy and flexible fashion. For training, there can be first purchased a number of training devices, and later, if the need arises, the system can be completed with the computer unit and connector element, as well as the required measuring programme and special programmes.

Yet another advantage of the invention is that by the aid of the connector element to be attached to an independent training device, the collecting and preprocessing of the measuring data are carried out in the immediate vicinity of the measuring location, in which case the possibility of electrical disturbances is minimized. Moreover, the electrical safety of the system is maintained on a high level. The connector element and the data processing unit are most advantageously separated galvanically. In addition to this, the system is independent of the detailed structure of the employed data processing unit.

Furthermore, the invention allows for a wide range of measurements. The measurement data is advantageously gathered from five different channels, and from this data there is automatically calculated several variables and indices describing strength, fitness, muscular type etc.

Moreover, the variables and indices calculated according to the invention can be stored in the memory of the data processing unit, where they can be processed statistically in large groups.

Another advantage of the invention is that the whole measuring process can be stored into the memory individual by individual, and can at any time be looked up and reanalyzed as a whole.

Further, owing to the invention the measuring data is gathered on the different channels in real time. All information is registered with the same time code, and can be surveyed simultaneously.

Another advantage of the invention is that the results from the measurement are clear and easy to read. The information from the measuring process, as well as the obtained results, are presented on the display screen during the measurement.

Another advantage of the invention is that on the same display screen there can be presented for instance information from two different measurements, such as the first and last measurement, and the results can be compared both graphically and numerically. Thus the outcome of the training is easily estimated. At the same time, an illustrative and understandable way of representation also encourages the individual to try and make progress in the training of muscular fitness.

Another advantage of the invention is that the results obtained from the measurements, for example from long series of fatigue tests, can be observed in detail, repetition by repetion, with a given area rescaled in an illustrative fashion.

In addition to this, owing to the present invention, the measurements and training strongly support each other. The measurements are performed with the same system as the training.

Another advantage of the invention is that the system is automatically ready for measurement as soon as its components are interconnected.

Yet another advantage of the invention is that by means of a single connector element, any suitable training device can be connected to the data processing unit.

Yet another advantage of the invention is that the types of the training device sensors are limited, so that the connecting of a training device to the connector element and further to the data processing unit is easily controllable both physically and programmewise.

Moreover, the measuring and training system of the present invention is easy to maintain, owing to its modular structure.

Yet another advantage of the invention is that it is economic as for the production costs. Moreover, the invention enables a flexible expansion of the system at moderate costs.

The invention is explained in detail below, with reference to the appended drawings, where

FIG. 11 illustrates the display a dynamic fatigue test, where

Figure 1:
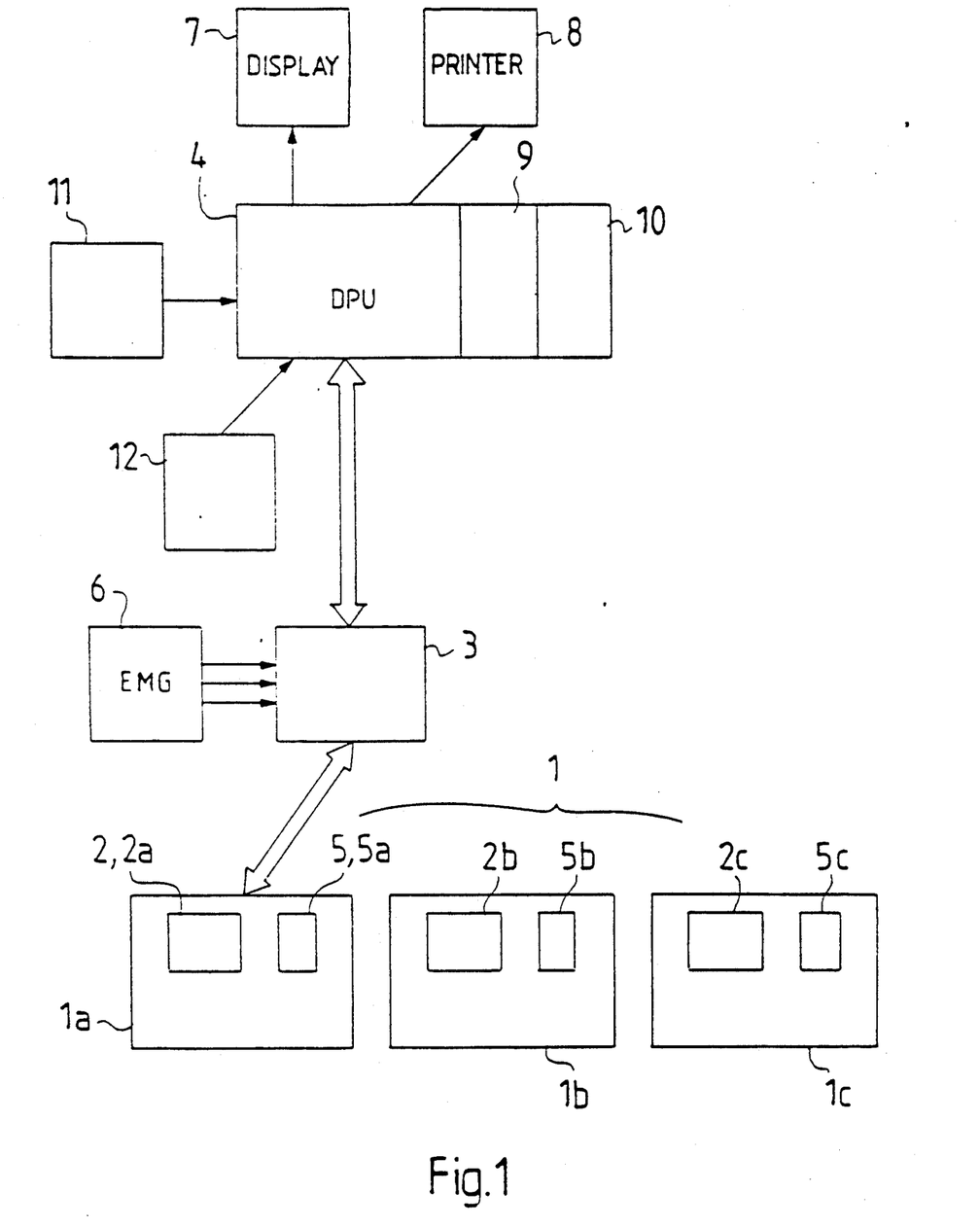
FIG. 1 illustrates the system of the invention as a block diagram.

The measuring and training system for measuring muscular functionality and for muscle training is schematically illustrated in the block diagram of FIG. 1. The system comprises mechanical devices whereby the muscles are loaded. The mechanical devices are training devices 1; 1a, 1b, 1c, and they are independent, separate devices provided with sensors 2; 2a, 2b, 2c. In addition, the system comprises a connector element 3 and a data processing unit 4. The connector element 3 is connected to the data processing unit 4. The sensors 2a of the training device 1a in question are connected to the connector element 3. In connection with the training device 1; 1a, 1b, 1c and the connector element 3, there are provided the identification means 5; 5a, 5b, 5c, whereby the type of the training device (1; 1a, 1b, 1c) to be used is identified. In addition to this, a number of sensors 6 measuring EMG is connected to the connector element 3. The display unit 7 and the printer unit 8 are connected to the data processing unit 4. Moreover, the data processing unit 4 is provided with a mass storage 9, such as a hard disk unit, and a floppy disk drive 10. The keyboard 11 and the mouse 12 are also connectable to the data processing unit 4.

Figure 2:
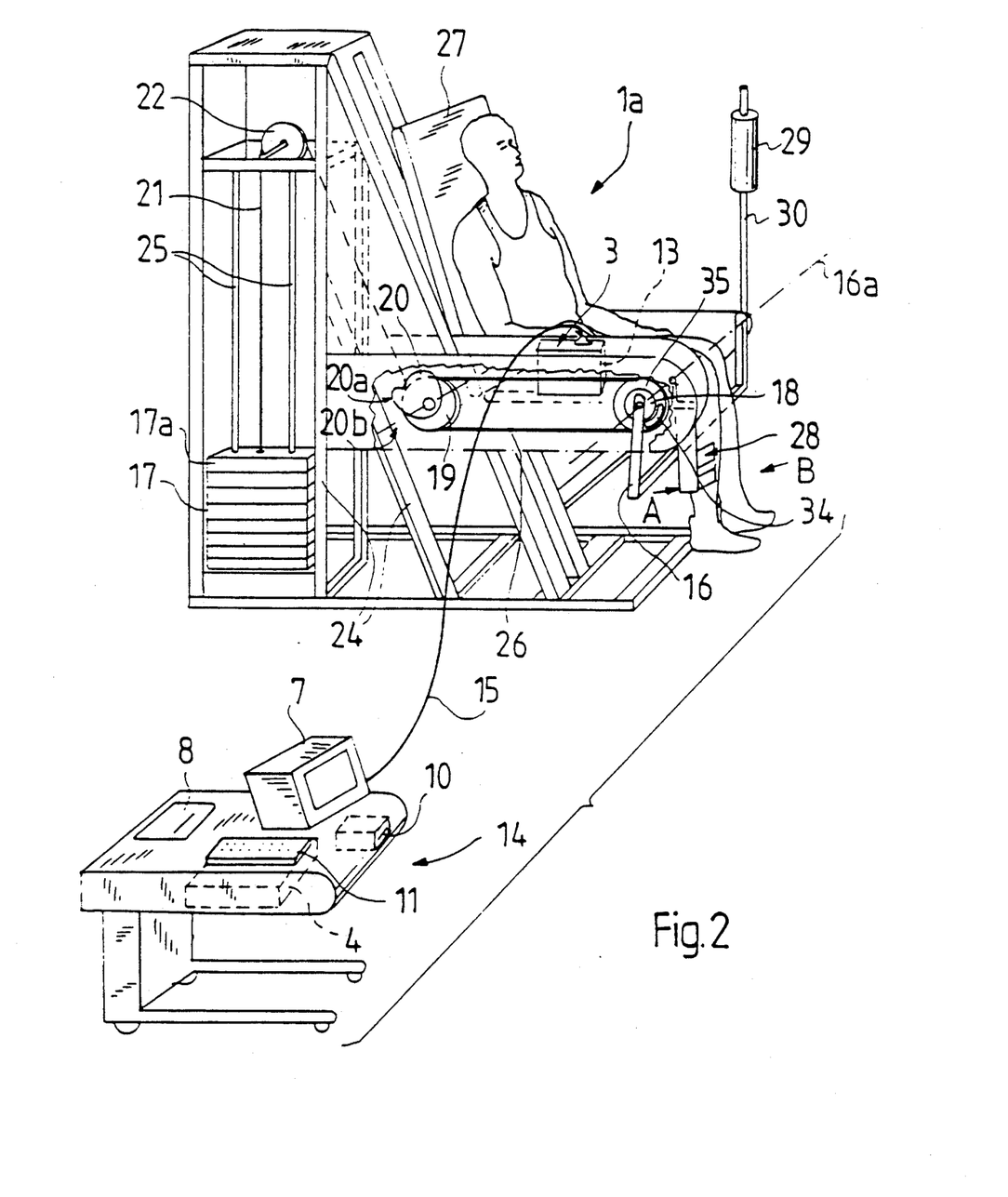
FIG. 2 illustrates a training system according to the invention, where the training device is a device designed for the measuring and training of the knee.
Figure 3:
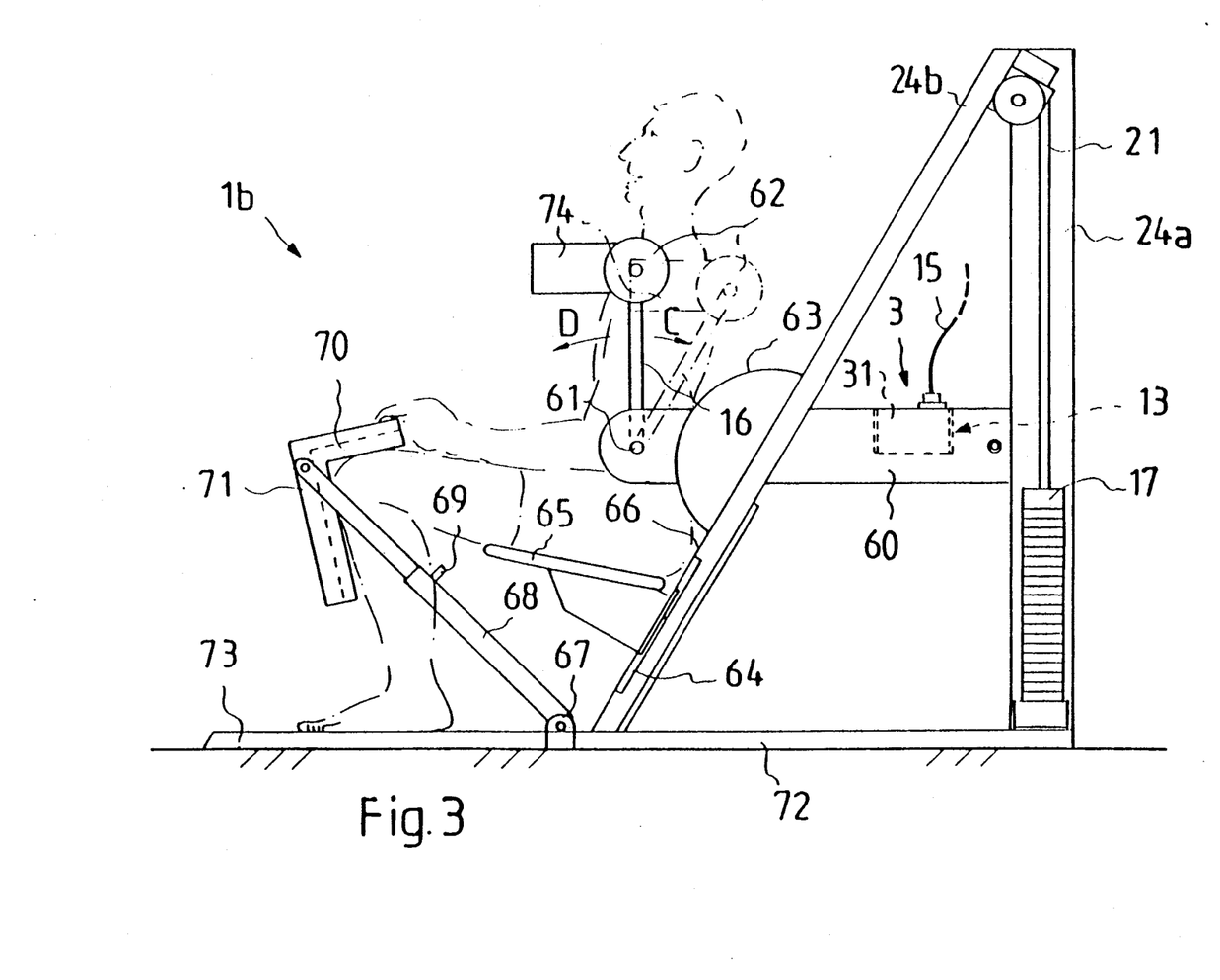
FIG. 3 illustrates, in partial cross-section, another training device which can alternatively be connected to the system of the invention.

A preferred embodiment of the measuring and training system of the present invention is illustrated in FIG. 2. In this case the training device 1a is a device for the training of the knee. FIG. 3 illustrates another training device 1b, which is designed for the training of the back and stomach muscles. It can also be connected, as an alternative to the training device 1a for example, to the system of FIG. 2.

The training device 1a includes a load, such as a counterbalance weight 17, which is subjected to gravitation, a lever arm 16, which is moved by the muscles to be measured and trained; and a transmission assembly, whereby the lever arm 16 is connected to the counterbalance weight 17. The counterbalance weight 17 is formed of a number of separate weight units 17a, a desired number whereof can be connected to the transmission assembly. Most advantageously, the counterbalance weight 17 is arranged to move vertically along the guides 25.

In this preferred embodiment, the transmission assembly is formed of two wheels 18, 19, such as cog-wheels or the like, and a connecting power transmission member 26, such as non-skid belt, advantageously cogged belt or chain. In connection to the first wheel 18, there is attached a lever arm 16. In connection to the second wheel 19, there is provided an eccentric 20. The power transmission member 21, such as a belt or chain, is at its first end connected to the eccentric 20, and at its second end to the counterbalance weight 17 via the cog-wheel 22. The power transmission assembly is suitably installed in connection with the frame 24 of the training device 1a.

The lever arm 16 is turnably fastened to the frame 24 and in a stationary fashion to the wheel 18 of the transmission assembly. By turning the lever arm 16, the second wheel 19 and further the eccentric 20 are manipulated via the first wheel 18 and the belt 26. The form of the guide surface 20a of the eccentric 20, i.e. the variation of the distance between the coordination point 20b and the guide surface 20a, is determined according to those muscles and joints that are meant to be trained and measured with the training device 1a. Thus the distance of the power transmission member 21, or the distance of the imaginary continuation in its line, from the coordination point 20b of the eccentric 20 determines the force whereby the counterbalance weight 17 can be hoisted by means of the lever arm 16. By means of the eccentric 20, it is possible to realize, in a simple fashion, an optimal physiological load in a training and measuring situation for each muscle group to be trained and measured.

Advantageously the eccentric 20 can be provided with two different guide surfaces, which are meant for the exercises and measurements of both extensors and flexors. In that case the eccentric 20 includes two eccentric guide surfaces, the starting points whereof are interlinked by means of connecting surfaces, so that the power transmission member 21 is shiftable from one guide surface to the other. This kind of arrangement is introduced in the Finnish patent application 874028.

The training device 1a of FIG. 2 is designed for the measurement and training of the muscles attached to the knee joint, as was stated above. Thus the training device 1a is provided with a seat 27, the front edge whereof is arranged near the turning axis 16a of the lever arm 16. The person sits on the seat 27. The leg under measurement is attached to the fastening device 28, which comprises for instance a chute-like element which is fitted and fastened underneath the knee. The fastening member 28 is connected to the lever arm 16. It may also be suitably articulated to the frame 24 of the training device 1a. Consequently the individual can be attached to the training device in a solid fashion and it can be secured, that the limb under measurement can be used only for performing the desired motions with the training device.

The lever arm 16 of the training device 1a also can be provided with a balance weight 29. The balance weight 29 is fitted to the bar 30, movably in the lengthwise direction thereof. The bar 30 is connected, via the turning axis 16a, to the lever arm 16, to the opposite side thereof. By means of the balance weight, the limb in question can be balanced to be weightless. Then the person can move the leg with his own muscular force, for example when the mere weight of the leg itself is too much for the muscles to move. The balance weight 29 makes it possible to measure muscular functionality, design a training programme and do exercises even in cases when the muscles and the knee joint are for instance severely damaged as a result of an accident.

The training device 1b of FIG. 3 is designed for measuring and training the back and stomach muscles. It comprises the frame 24a, in connection whereof there is provided a counterbalance weight 17, which is subjected to gravitation; a lever arm 16, which is moved by the muscles to be measured and/or trained; and a transmission assembly, whereby the lever arm 16 is connected to the counterbalance weight 17. The transmission assembly and the fastening of the lever arm are for instance similar to those in the training device 1a of FIG. 2. Generally speaking, the same reference numbers are used of like parts of the training devices in FIGS. 2 and 3.

The frame 24a includes an inclined member 24b, and horizontal casings 60 on both sides of the frame. Through the transmission means and the frame 24a, for instance through one of the horizontal casings 60, the counterbalance weights 17 are connected to the lever arms 16 geared to the ends of the casings 60. The lever arms 16, directed outwards from both casings at the gearing points 61, are connected to each other at their heads by means of a support roller 62, which forms a transversal, horizontal support extending over the whole width of the apparatus.

The inclined member 24b of the frame 24a comprises a convex surface 63, which in the horizontal direction is an essentially straight and even, vertically curving surface, advantageously part of a cylinder mantle, which extends over the whole width of the apparatus in between the casings 60. Below the convex surface 63, in the inclined member 24b, there is attached, by means of an adjusting device 64, a seat 65 adjustable in height, so that the inclined member 24a forms a back rest 66 in between the seat and the convex surface 63.

At the bottom part of the frame 24a, below the seat 65, there is attached, by means of an articulation 67, an elongate arm 68, whereto a knee support 71 provided with padding 70 is attached by means of an adjusting member 69. By applying the adjusting member 69, the knee support is attachable at various heights to the arm 68. In addition to this, the apparatus comprises a foot rest 73 as a forward protruding continuation of the bottom part 72 of the frame.

The training device of the above described type is introduced in the Finnish patent application 890,581.

The device of FIG. 3 is operated as follows. The person sits on the seat 65, the height whereof is adjusted to be suitable so that the hip area can be supported against the back rest 66 in between the seat 65 and the convex surface 63. The location of the gearing point 61, with respect to the back, is attempted to be set, by means of the said adjustments, so that the articulation point is in the area between the third and fifth lumbar vertebra. Thereafter the knee supports 71 are placed in connection with both knees and locked into place, so that they hold and press the knees, and through the knees, the thighs, and further, essentially parallel to the thighs, the hips against the seat and the back rest. Thus the hips are locked as immobile and unturnable against the back rest, in between the seat and the convex surface. When the upper part of the body is bent backwards in the direction C (cf. the dotted lines), the back is bent and supported against the convex surface 63, and simultaneously the shoulder area is supported against the support roller 62, which creates the opposite force resisting the motion.

The training device 1b of FIG. 3 is made to operate as a measuring and training device for the stomach muscles by connecting, for instance with the fastening member 74, the lever arms 16 and the support roller 62 suitably to the upper part of the body, and by arranging a suitable load via the transmission means. In this case the eccentric 20 of the transmission assembly is provided with two guide surfaces, one of which is meant for the training and measurements of the back muscles, and the other for the training and measurements of the stomach muscles. By bending the body forward in the direction D, the stomach muscles must exert while the body is bent against the opposite force opposing the motion obtained via the lever arms 16.

The independent, separate training devices 1; 1a, 1b, 1c, to be connected to the measuring and training system of the invention most advantageously include at least the following elements: a load such as a counterbalance weight 17, which is subjected to gravitation, and the size whereof can be suitably chosen; at least one lever arm 16, which is moved with the muscles under measurement, and a transmission assembly, wherethrough the lever arm 16 is connected to the counterbalance weight 17. The training devices 1; 1a, 1b, 1c (FIG. 2 and 3) are dissimilar in the sense how the extremities, trunk and parts thereof, as well as the connected muscles to be measured and trained, can be attached to the lever arm 16. When each limb has its own training device, the individual can be securely fastened to the device so that the connecting of the lever arm 16 to the muscles to be measured can be carried out correctly from the biomechanical and ergonomical point of view, and so that by means of the device it is possible to perform only the desired motions. Thus the measuring process is always carried out in conditions as similar as possible to the training programme defined by the measurements.

Figures 4, 5, 6:
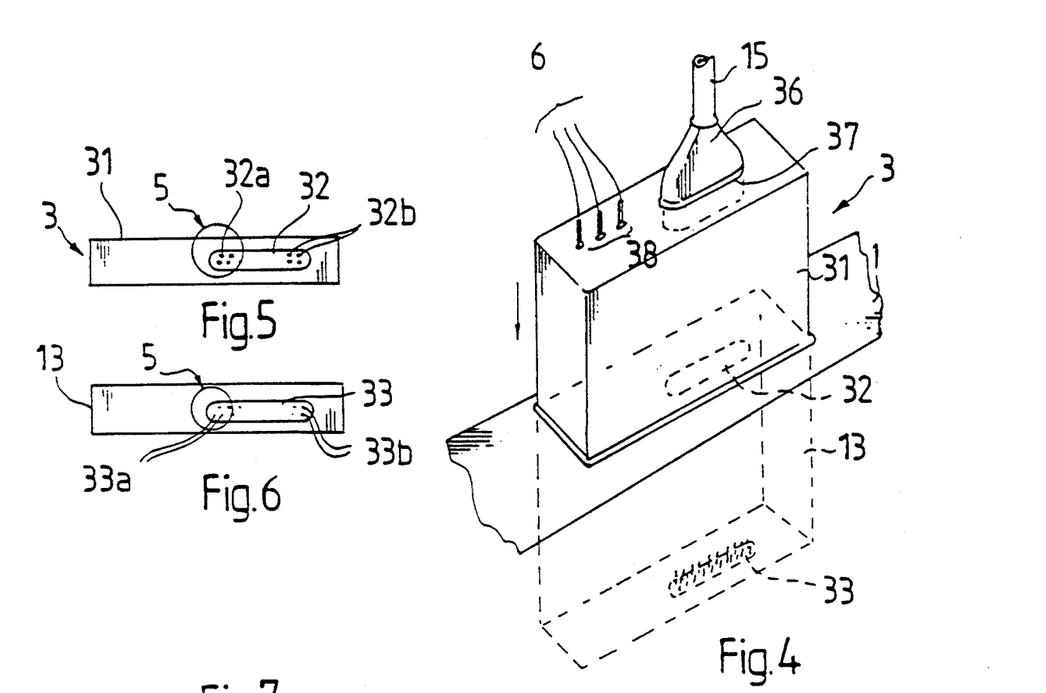
FIG. 4 illustrates the connector element and nest connected to a preferred embodiment of the invention.
FIG. 5 illustrates the corresponding connector element as seen from one direction.
FIG. 6 illustrates the bottom of the nest.
Figure 7:
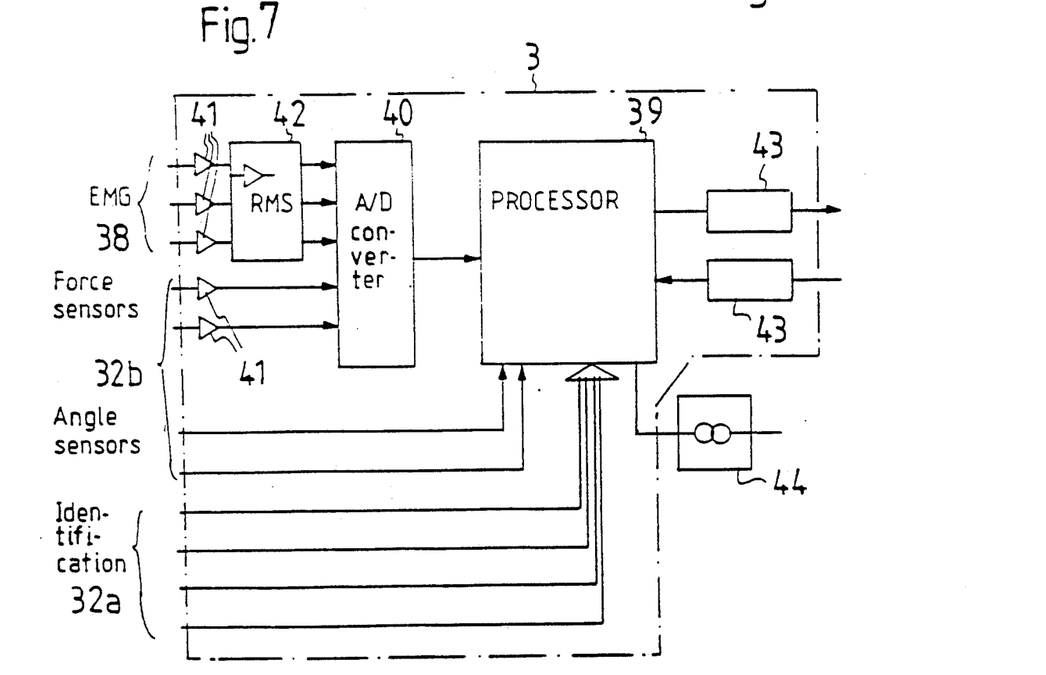
FIG. 7 illustrates the connector element, according to a preferred embodiment of the invention, in the form of a block diagram.

Most advantageously the connector element 3 is an independent device which is installed in its own casing 31, as is illustrated in FIG. 4. Each training device 1; 1a, 1b, 1c, is provided with the nest 13. The connector element 3 together with the casing 31 can be detachably installed in the nest 13 of the training device 1. The connector element 3 and the nest 13 are provided with matching linking parts 32, 33. The sensors 34, 35 of the training device 1 are connected to the linking part 33 provided in connection with the nest 13. The connector element 3 in turn is connected by a coupling cable 15 to the data processing unit 4. The connector element 3 and the coupling cable 15 are provided with linking parts 36, 37 for connecting them together. The data processing unit 4, together with connected equipment, of which FIG. 2 represents the display 7, printer 8 and keyboard 11, is placed in a movable carriage 14. The data processing unit 4 is connected to the connector element 3 by means of a coupling cable 15.

The identification means 5; 5a, 5b, 5c (FIG. 1) are in the embodiment of FIGS. 2, 3 and 4 formed of a group of mechanically interconnected parts, such as protuberances, pins or spikes, and corresponding apertures, which are provided in the connector element 3 and the training device 1. The respective parts connected to each training device 1; 1a, 1b, 1c (FIG. 1) are coded as for order and/or number in a way characteristic to the specific training device in question, and thus the training device can be identified.

The identification means 5 are advantageously arranged in connection to the matching linking parts 32, 33 of the training device 1 and the connector element 3. Part of the spikes 32a of the linking part 32 of the connector element 3 are reserved for the use of the identification means, and respectively part of the corresponding apertures 33a of the linking part 33 of the training device 1; 1a, 1b, 1c are also reserved for the use of the identification means 5. The rest of the spikes 32b and apertures 33b of the linking parts 32, 33 are reserved for connecting the sensors 34, 35 of the training device 1; 1a, 1b, 1c electrically to the connector element 3.

The sensors 34, 35 of the training device 1, 1a (FIG. 2) include load sensors 34, such as strain gauge sensors, and range of motion sensors 35, such as angle sensors.

The load sensors 34 are connected to the turning axis 16a of the lever arm 16, or to a respective point in the transmission assembly. The number of load sensors 34 is advantageously two, and they are used for measuring forces directed for instance to the opposite directions of the lever arm 16, either in direction A or direction B, or forces directed to two separate lever arms.

The range of motion sensors 35 are also connected to the turning axis 16a of the lever arm 16 or to a corresponding part in the transmission assembly, and they are used for measuring the angular position of the lever arm 16, as compared to a given initial angle. The training device 1b of FIG. 3 also includes the above mentioned sensors 34, 35, although they are not illustrated in the drawing. .. In addition to this, the connector element 3 is provided with a number, in this case three, of EMG sensors 6. These are connectable, via the connectors 38, to the connector element 3. The EMG sensors are attached to the skin surface in the vicinity of the muscles under measurement.

In FIG. 6, the connector element 3 is illustrated in the form of a block diagram. The connector element 3 comprises a processor 39, an analog to digital or A/D converter 40, a number of amplifiers 41, whereto the analogical sensors are connected, a RMS (Root-Mean-Square) indicator 42 and isolators 43, such as optoisolators. The EMG sensors 6 are connected, via the amplifiers 41 and the RMS indicator 42, to the A/D converter 40 and further to the processor 39. The analogical sensors, such as the load sensors 34, are connected, via the amplifiers 41 to the A/D converter 40 and further to the processor 39. The digital sensors, such as the digital angle sensors 35, are connected directly to the processor 39. The processor 39 is connected, via the isolators 43, in duplex operation to the data processing unit 4. The identification means 5 are also connected to the processor 39. To the connector element 3 there is fed required current from a suitable power supply 44, most advantageously via the coupling cable 15.

The data processing unit 4 is formed of a computer which has sufficient capacity for performing the measuring programme and for analysing the measuring information. In addition to this, the data processing unit 4 must be able to rapidly process programmes for special functions. Generally speaking, a suitable data processing unit is a quick microprocessor of the AT level.

In principle the system of the present invention operates as follows. Among a number of separate, independent muscle training devices 1; 1a, 1b, 1c (FIG. 1) there is chosen the training device 1a, whereby the muscles are loaded and the muscular functionality measured. The training device is chosen according to the muscles to be trained or measured; an example is the measuring and/or training device 1a for the knee in FIG. 2. The training device 1a to be used is connected to the data processing unit 4 by means of the connector element 3. This is carried out simply by inserting the separate connector element 3 into the nest 13 provided in the training device 1 (cf. FIG. 4). The linking parts 32, 33 of the connector element 3 and the training device 1 match and thus connect the sensors 34, 35 to the connector element 3 together with the identification means 5. By means of the data processing unit 4 and the connector element 3, the training device 1 is identified by making use of the said identification means 5.

After the training device 1a is identified according to the signal sent by the connector element 3 to the data processing unit 4, the corresponding measuring programme is automatically started. The measuring programme includes a number of measuring steps, among which the desired is chosen, and the initial settings defined for each person individually. The measuring programme is illustrated as a block diagram in FIG. 8, which is explained in more detail below, particularly when used together with the training device 1a of FIG. 2, i.e. the measuring and training device for the knee.

First the measuring programme checks that the information about the individual in question is stored in the personal data of the system. If not, the information of a new person is registered. The object of the measurement is defined, advantageously according to a menu, i.e. for instance in this case the programme asks whether to measure the right or the left leg, or both. When the choices are made, the programme proceeds to the measurement proper.

Figure 8:
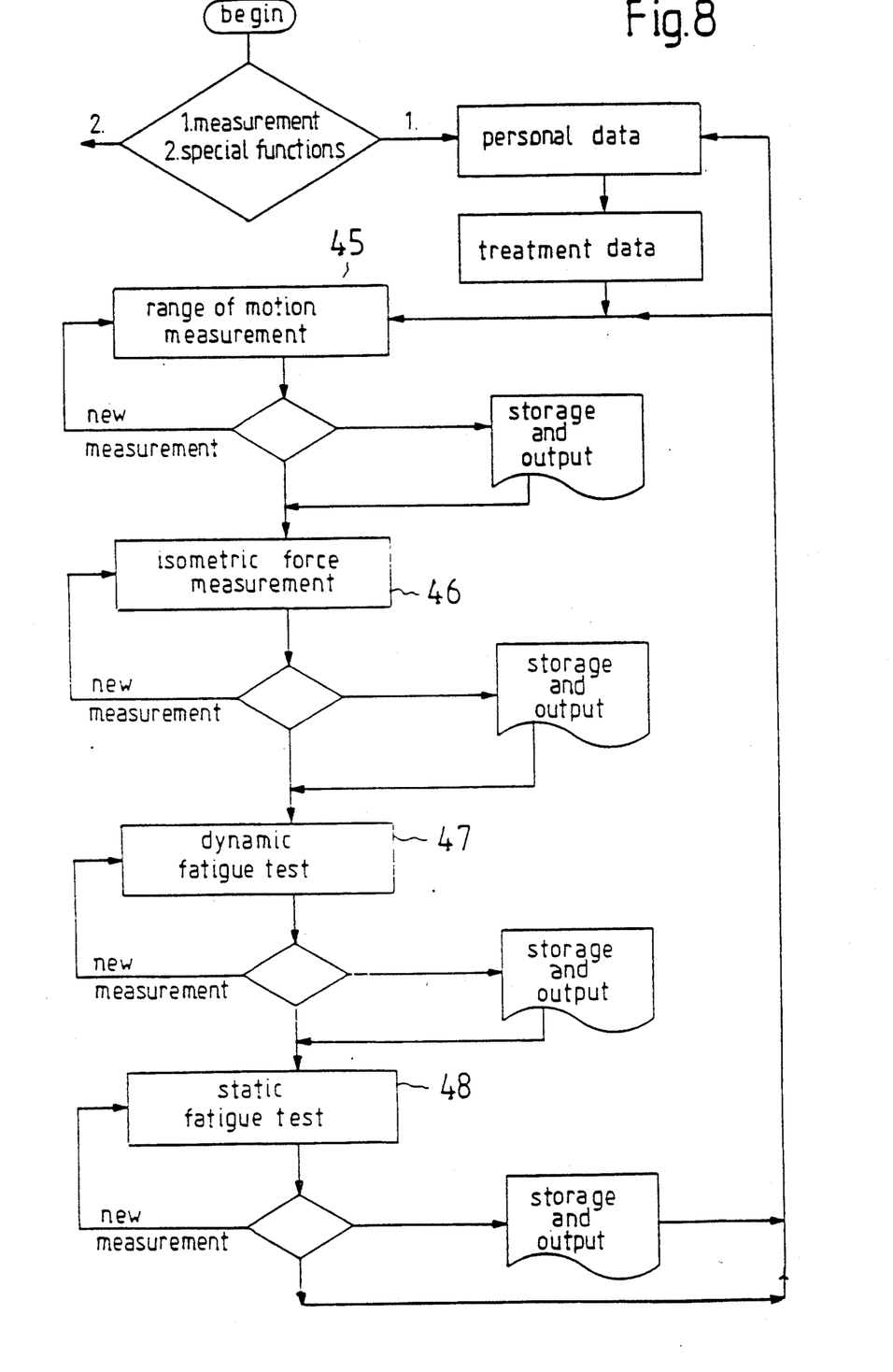
FIG. 8 illustrates the measuring programme according to a preferred embodiment of the invention in the form of a block diagram.

The measurements include a range of motion measurement 45, isometric force measurement 46 and a fatigue test, which is divided into dynamic fatigue test 47 and static fatigue test 48, as is illustrated in FIG. 8. The range of motion measurement 46 measures the ranges of motion of the joints as angles of rotation around suitable turning or articulation points.

In the training device 1a of FIG. 2, the range of motion measurement of the knee is carried out so that the lever arm 16 is moved with the muscles connected to the knee, by extending the leg and by flexing it between extreme positions, and by measuring the rotation of the lever arm 16 in angle degrees by means of the range of motion sensors 35.

The measurement is carried out in real time, and it can be presented on the display unit 7 simultaneously as it is being done. On the same scale of measurement there is displayed for instance the normal range of motion of the knee in degrees, and the motion of the lever arm 16 is observed as a parallel changing column, in which case any deviation from the normal is detected immediately.

Next the isometric force measurement 46 can be carried out. This measurement measures the torque, particularly the maximum torque. The force measurement is most advantageously performed in a static fashion, so that the lever arm 16 is maintained at a predetermined angular position, and while the muscles are being exerted, the torque directed to the lever arm 16 is measured. Simultaneously the activity of the muscles chosen around the knee is measured by means of the EMG sensors 6.

The measurement of the torque is carried out for the duration of a given period, such as 5 sec., after the torque caused by the muscles to the lever arm 16 has exceeded the preset limit value. The said limit for the knee is for instance 10 Nm. Thereafter there is calculated a highest short-time average for the torque, i.e. maximum torque. The whole measuring process can be replayed in real time on the display unit, together with the EMG signals of the muscles.

After the isometric force measurement, the next step is the fatigue tests, where the muscles are strained with a suitable standard load. The fatigue test can be performed either as dynamic 47 or static 48.

The dynamic fatigue test is carried out with a chosen standard load so that among a number of predetermined angular velocities, such as 60°/s, 90°/s or 120°/s, there is chosen a reference velocity for the test, whereafter this reference velocity is represented on the display unit 7 as a visually expanding and contracting column on a suitable angle scale, and the test is carried out by following this velocity, i.e. by turning the lever arm 16 with the muscles under measurement. The turning of the lever arm 16 is shown in real time on the display unit, beside a changing column representing the reference velocity.

The load of the dynamic fatigue test is advantageously chosen on the basis of the isometric force measurement, so that it corresponds to a given portion, such as 10% or 50%, of the maximum torque. Thereafter there is chosen the reference velocity for the test, in similar fashion as above, and the test is carried out.

After the dynamic fatigue test, there can be carried out the static fatigue test 48. The fatigue test is carried out with a chosen standard load, so that the standard load is maintained in a predetermined position, for instance in a given angular position, and the torque is observed and measured.

All of the above described measurements are alternative. According to the special needs, one or several measurements can be skipped and moved to the next, which is then performed. Each measurement can after performance be rejected, accepted or retried, and after acceptance stored and written out if necessary.

Simultaneously as muscular torque measurements are carried out, there can also be carried out EMG measurements in suitable muscles chosen beforehand. The obtained results can be shown directly in real time on a display unit, both digitally and graphically in various illustrative pictures. After performing the measurements, the results can be surveyed on the display unit by rescaling the measurements at the desired point.

Figure 9:
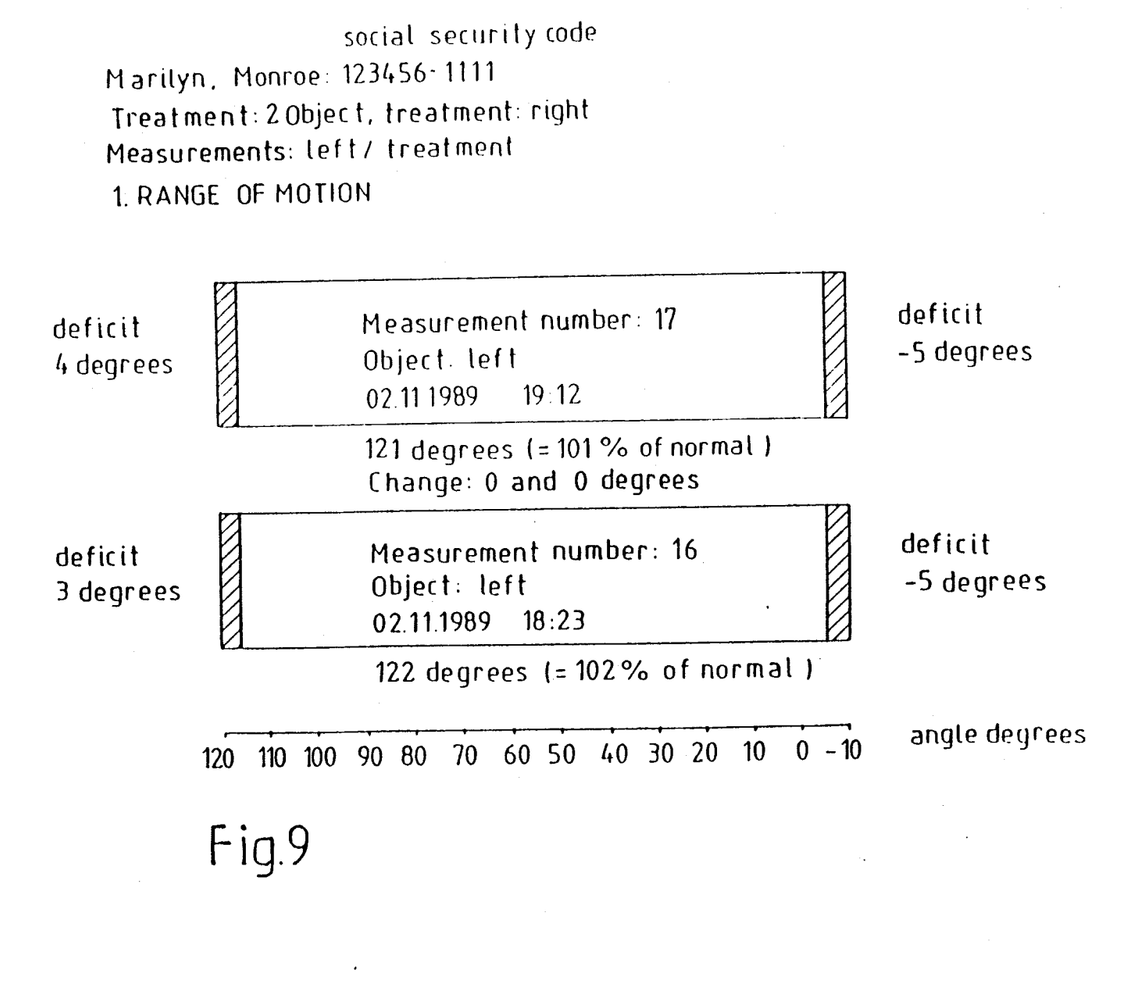
FIG. 9 illustrates the comparison of the results from two measurements of the range of motion.
Figure 10:
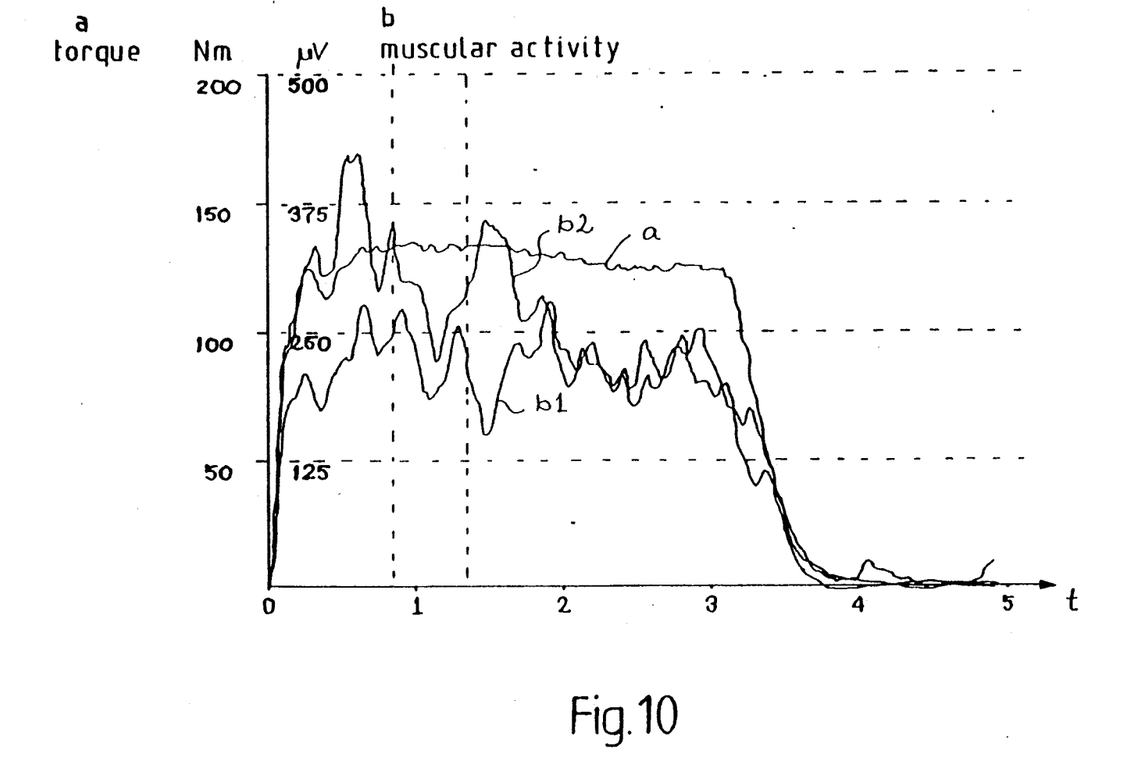
FIG. 10 illustrates the display an isometric force measurement.

FIGS. 9, 10 and 11 illustrate various ways of writing out the obtained results. In FIG. 9, the results from two separate range of motion measurements are compared.

For instance the measurements carried out at the beginning of the therapy are compared to the measurements carried out during training, and the representation of both measurements on the same print or screen gives a clear idea of the development and success of the training.

All performed measurements can be compared to each other. Measuring information is stored, in connection to the measurements, in the mass storage 9 of the data processing unit 4, and on the diskettes for each person in the floppy disk drive 10. Detailed measuring information can be looked up one by one from the memory and analysed repetition by repetition, for example by rescaling the measurement (cf. FIG. 10). If desired, suitable prints of the comparison between measurement results are obtained from the printer 8.

The method of displaying the isometric force measurement is illustrated in FIG. 10. In addition to the force measurement proper, there is measured the electric activity of the muscles by means of the EMG sensors 6 on three different channels, and the average maximum values in microvolts are expressed as separate indices. The curves are illustrated on the same time scale t. By means of the EMG curves of the muscles, it is possible to actively define the level of exertion and its relation to the force (EMG/max M). The calculated indices give information of velocity, relative force and strength level in relation to the loading of the training device. It is advantageous to reproduce the curves in different colours both on the display screen and on a paper print, so that they are clear and easily readable.

Figure 11A:
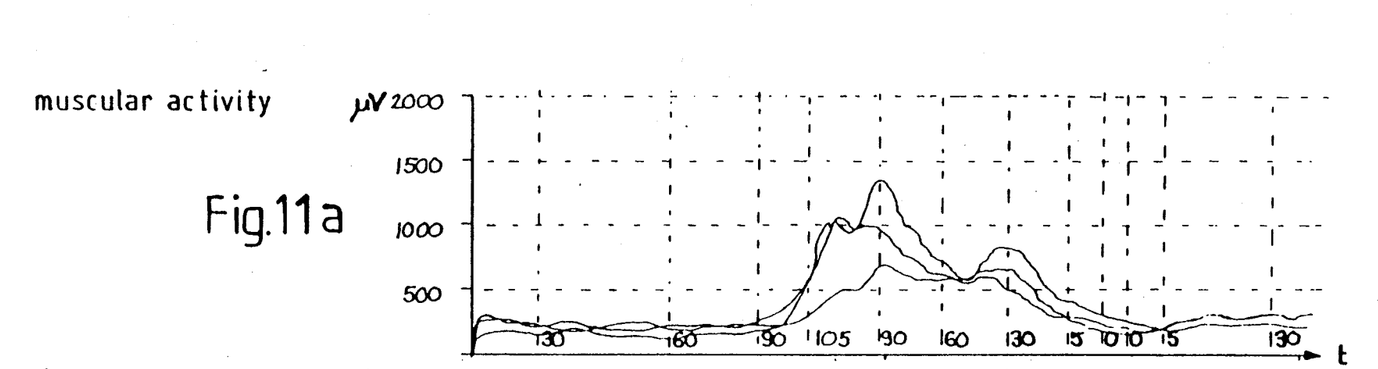
FIG. 11a illustrates the EMG curves.
Figure 11B:
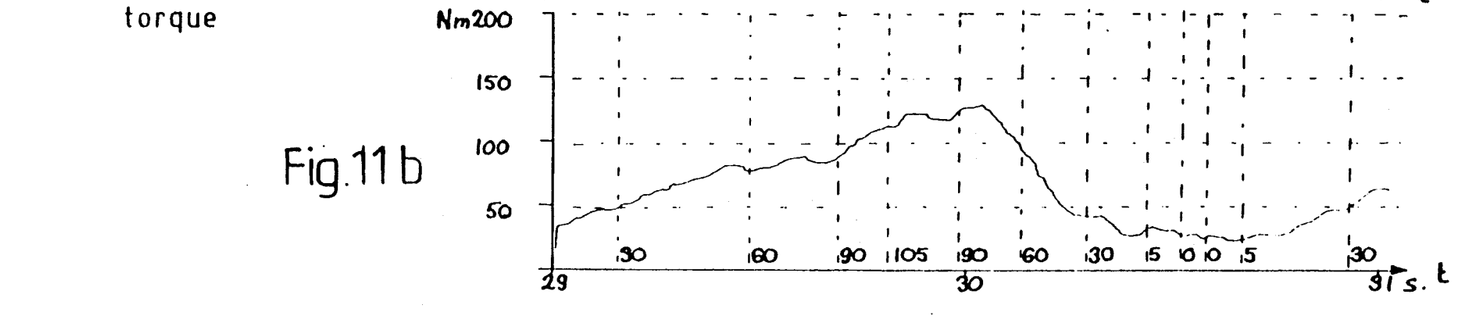
FIG. 11b illustrates the strength curve as a function of time.
Figure 12:
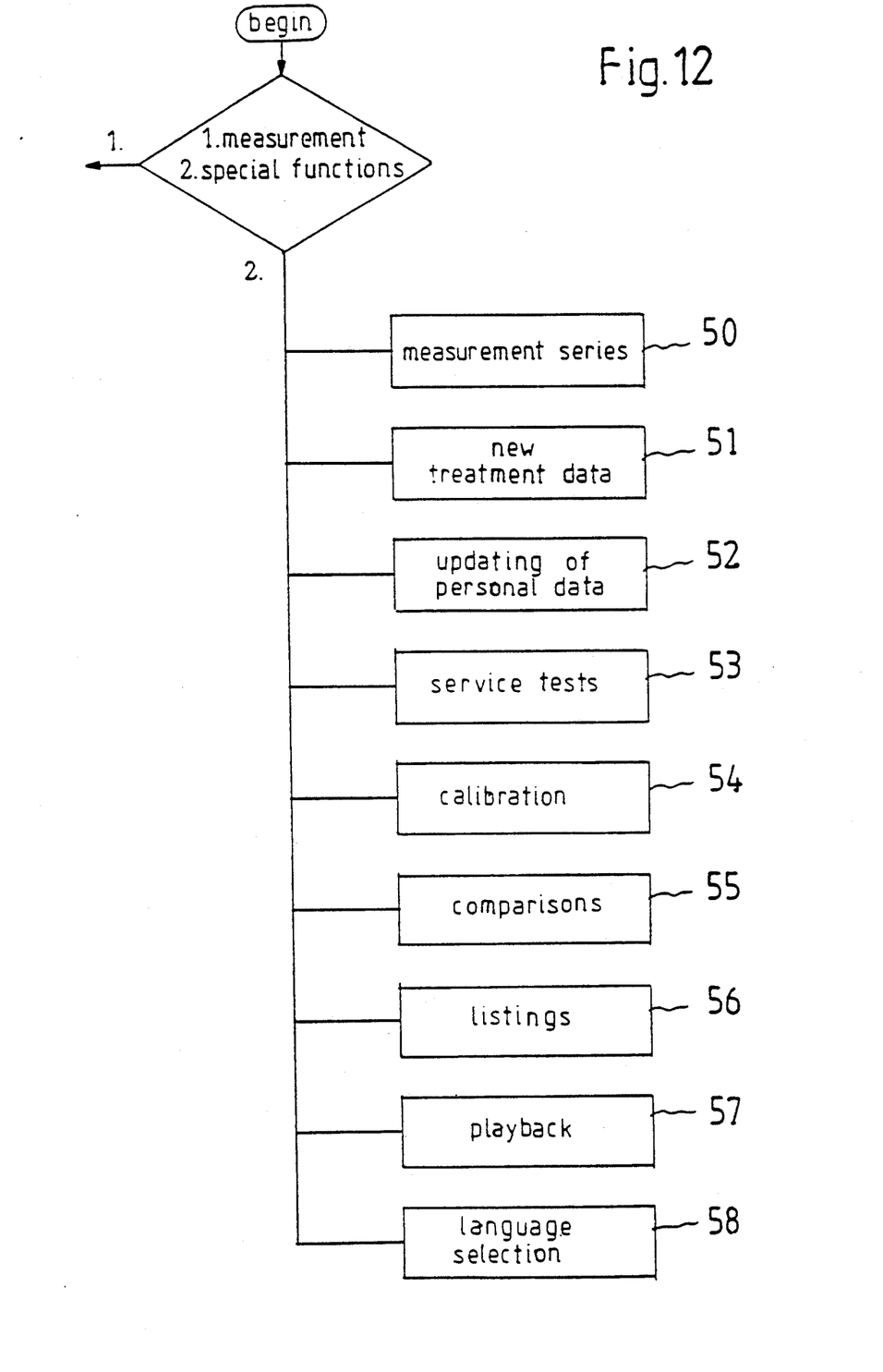
FIG. 12 illustrates in block diagram form the special function programmes connected to a preferred embodiment of the invention.

An example of displaying the dynamic fatigue test is illustrated in FIG. 11. The EMG curves representing three different muscles are illustrated in FIG. 11a, and the corresponding force curve in FIG. 11b. Each curve is illustrated as a function of time t and so that the scale of measurement, in this case time-scale, is zoomed from two seconds at a suitable point of the measurement, to 29–31 sec. The angle markers, which are illustrated with vertical dotted lines, point at knee angles of 30°, 60° and 90°, as well as the extreme positions. The use of the time scale makes it possible to examine the variables simultaneously and for instance to find out the point of motion where the muscles are activated.

In addition to the measuring programme described above, optional special functions can be chosen when desired, these being illustrated in the block diagram of FIG. 11. By using the special function programmes, there can be performed the following operations: measurement series 50, registering new operational data 51, updating personal data 52, service test measurements 53, sensor calibration 54, comparison of obtained results 55, listings of obtained results 56, playback of the obtained results and selection of the language to be used in the system.

By means of the measurement series 50, it is possible to compile beforehand the series of activities to be performed in the measurement. This kind of measurement in series pertains for instance to muscular functionality measurements connected to the functionality of the muscles of the right knee, so that the measuring programme includes the range of motion measurement, the isometric force measurement, the dynamic fatigue test where the load is determined to be 60% of the measured maximum isometric torque at the velocity 90°/s and which measurement also measures the EMG of two defined muscles simultaneously.

In the new treatment data 51, it is possible to give a new code number for a person who already has a code number in the system. This may be necessary if the same person is subjected to muscular functionality measurements of muscles located in different parts of the body, and with different training devices.

In the updating of personal data 52 it is possible to change the information of each individual.

In the service test 53, the data processing unit 4 is used for checking the electric components of the system and for reporting detected malfunctions.

By means of the calibration function 54, the real offset voltages of the EMG amplifiers are checked and trimmed to zero.

By means of the comparison functions 55, the information obtained in different measurements can be observed simultaneously.

By means of the listing functions 56, the personal data can be surveyed in three different ways. The list of individuals gives the names of each person in alphabetical order, and some additional basic information can be given. The treatment list lists the persons in alphabetical order with each treatment. On the basis of the measurement list, it is possible to survey measurement information of all individuals, of selected measurements of one single person, or of one single measurement of several selected persons.

By means of the playback functions 57 of the measuring data, the obtained results can be surveyed in exactly the same form as they were presented after the measurement. The results can be analyzed in similar fashion as in connection with the measurements proper.

By means of the language selection function 58, there can be chosen the language for conversing with the system and for writing out the documents. The conversation language and documentation language can be chosen irrespective of each other. The general alternatives are English, German, French, Swedish or Finnish.

In the above specification, the measuring operations are explained with reference to the training device 1a of FIG. 2. It is apparently clear that similar measurements can also be carried out with the training device 1b of FIG. 3, where the lever arm 16 is moved by means of the back and/or the stomach muscles.

The invention is not limited to the above described performed embodiments only, but many modifications are possible without departing from the inventional idea defined in the patent claims.

We claim:

1. A method for measuring the working condition of muscles, wherein muscles are placed under load by mechanical training devices, the working condition of the muscles is measured, and the results obtained are registered, comprising the steps of:
   providing a mechanical training device for placing the muscles of a subject under load, and for measuring the working condition of the muscles;
   providing a data processing unit having a measuring program corresponding to said mechanical training device and including a plurality of measurements of the working condition of the muscles;
   connecting said data processing unit to said mechanical training device;
   identifying said mechanical training device for said data processing unit; and
   activating said measuring program to obtain a desired measurement of the working condition of the muscles, wherein said load is generated by said mechanical training device by a counterbalance weight, and said load is opposed by the action of the subject against a balanced lever arm, and wherein said plurality of measurements of the working condition of muscles includes a range of motion measurement, wherein the ranges of motion of the joints of the extremities are measured as angles of rotation; an isometric force measurement, wherein the variable measured is torque; and a fatigue test, wherein the muscles are strained by a standard load.

2. The method as claimed in claim 1 wherein said isometric force measurement is carried out statically, said lever arm being maintained at a predetermined angular position, the torque directed to said lever arm being measured statically.

3. The method as claimed in claim 2 wherein the measurement of the torque is made during a set interval after the torque has exceeded a preset limit value, and the maximum short-period average for the torque is determined.

4. The method as claimed in claim 1 wherein the fatigue test is carried out dynamically with a standard load at a reference angular velocity chosen from a plurality of predetermined angular velocities.

5. The method as claimed in claim 1 wherein the fatigue test is carried out statically with a standard load, wherein the standard load is maintained in a predetermined position by the muscles while the torque is measured.

6. The method as claimed in claims 4 or 5 herein the standard load used in the fatigue test is determined on the basis of the results of the isometric force measurement for maximum torque.

7. The method as claimed in claim 1 wherein said plurality of measurements of muscular functionality are made while measuring the electrical activity of the muscles.

8. The method as claimed in claim 1 further comprising the step of displaying the results of the measurements on a display unit.

9. The method as claimed in claim 1 further comprising the step of surveying the results of the measurements on a display unit by rescaling the measurements at a desired point.

10. The method as claimed in claim 1 further comprising any step in the group of steps consisting of:
    setting up a measurement series from said plurality of measurements of the working condition of muscles;
    entering new operational data into said data processing unit;
    updating personal data in said data processing unit;
    conducting service test measurements;
    carrying out sensor calibrations;
    comparing the results of measurements made at different times;
    listing the results obtained in measurements;
    recalling and evaluating the measuring data; and
    selecting the language to be used by the data processing unit.

11. A measuring and training system for measuring the working condition of muscles and for the training of muscles, said system comprising at least one mechanical device for measuring the working condition of muscles, a data processing unit whereto the results obtained in measuring the working condition of muscles are transferred and whereby the results are analyzed, and means for displaying information obtained by analyzing said results wherein said at least one mechanical device is a training device having a load sensor and a range of motion sensor, wherein said system further comprises a connector element for joining said at least one mechanical device to said data processing unit, said connector element being connectable to said load sensor and said range of motion sensor, and wherein said at least one mechanical device has an identification means by which it may be identified through said connector element to said data processing unit.

12. The system as claimed in claim 11 wherein said training device has a counterbalance weight serving as a load, and comprises at least one lever arm connected to said counterbalance weight through a transmission assembly, said at least one lever arm being moved by a subject the working condition of whose muscles is to be measured.

13. The system as claimed in claim 12 wherein said connector element comprises a processor and an analog-to-digital converter, said load sensors being connected to said processor through said analog-to-digital converter, said processor being connected to said data processing unit via at least one isolator.

14. The system as claimed in claim 11 wherein said connector element may be detachably fastened to said training device.

15. The system as claimed in claim 14 wherein said training device is provided with a nest, said connector element being installable within said nest, said nest and said connector element having matching male/female linking parts, whereby said load sensor and said range of motion sensor may be electrically connected to said connector element.

16. The system as claimed in claim 14 wherein said identification means are included in said training device to identify said training device to said data processing unit through said connector element.

17. The system as claimed in claim 13 wherein said load sensors are strain gauge sensors, and said range of motion sensors are angle sensors.

18. The system as claimed in claim 13 wherein said connector element further comprises a plurality of sensors for measuring the electrical activity of muscles.

* * * * *